US010426804B2

(12) United States Patent
Izawa et al.

(10) Patent No.: US 10,426,804 B2
(45) Date of Patent: Oct. 1, 2019

(54) PENTOSIDINE PRODUCTION INHIBITOR

(71) Applicant: Kabushiki Kaisha Yakult Honsha, Minato-ku (JP)

(72) Inventors: Naoki Izawa, Tokyo (JP); Daisuke Niwa, Tokyo (JP); Toshiro Sone, Tokyo (JP)

(73) Assignee: Kabushiki Kaisha Yakult Honsha, Minato-ku (JP)

( * ) Notice: Subject to any disclaimer, the term of this patent is extended or adjusted under 35 U.S.C. 154(b) by 0 days.

(21) Appl. No.: 14/902,668

(22) PCT Filed: Jun. 25, 2014

(86) PCT No.: PCT/JP2014/066799
§ 371 (c)(1),
(2) Date: Jan. 4, 2016

(87) PCT Pub. No.: WO2015/002043
PCT Pub. Date: Jan. 8, 2015

(65) Prior Publication Data
US 2016/0166622 A1 Jun. 16, 2016

(30) Foreign Application Priority Data
Jul. 5, 2013 (JP) ................. 2013-141347

(51) Int. Cl.
| A61K 35/744 | (2015.01) |
| A61K 35/20 | (2006.01) |
| A61K 36/886 | (2006.01) |
| A23C 9/123 | (2006.01) |
| C12P 1/04 | (2006.01) |
| A23L 5/20 | (2016.01) |
| A23L 33/135 | (2016.01) |

(52) U.S. Cl.
CPC .......... *A61K 35/744* (2013.01); *A23C 9/1238* (2013.01); *A23L 5/28* (2016.08); *A23L 33/135* (2016.08); *A61K 35/20* (2013.01); *A61K 36/886* (2013.01); *C12P 1/04* (2013.01); *A23Y 2240/75* (2013.01)

(58) Field of Classification Search
CPC .... A61K 35/744; A61K 35/747; A61K 35/20; A23L 33/135; A23L 5/28; C12P 1/04; A23C 9/1238; A23C 9/127; A23Y 2240/75
See application file for complete search history.

(56) References Cited

U.S. PATENT DOCUMENTS

| 7,524,504 B1 * | 4/2009 | Bishop | A61K 8/645 424/195.15 |
| 8,088,369 B2 * | 1/2012 | Izawa | A61K 8/99 424/70.13 |
| 8,591,882 B2 * | 11/2013 | Izawa | A61K 8/99 424/780 |
| 9,439,933 B2 * | 9/2016 | Masuoka | |
| 2002/0016284 A1 * | 2/2002 | Perry | A61K 49/0004 514/1 |
| 2010/0291049 A1 * | 11/2010 | Izawa | A61Q 19/08 424/93.44 |
| 2013/0095073 A1 * | 4/2013 | Masuoka | A61K 31/702 424/93.3 |
| 2013/0164399 A1 * | 6/2013 | Izawa | A61K 8/99 424/780 |

FOREIGN PATENT DOCUMENTS

| JP | 61-53217 A | 3/1986 | |
| JP | 2000 264811 | 9/2000 | |
| JP | 2002 241293 | 8/2002 | |
| JP | 2004 196664 | 7/2004 | |
| JP | 2004 300153 | 10/2004 | |
| JP | 2006 256977 | 9/2006 | |
| JP | WO 2012026346 A1 * | 3/2012 | ............... A61K 8/99 |
| JP | 2013 75883 | 4/2013 | |
| KR | 970009620 B1 * | 6/1997 | |
| KR | 20120101897 A * | 9/2012 | |
| KR | 10-2012-0139916 A | 12/2012 | |
| WO | 2008 093670 | 8/2008 | |

OTHER PUBLICATIONS

KR 970009620 English abstract. Published Jun. 17, 1997. (Year: 1997).*
KR 20120101897 English abstract. Published Sep. 17, 2012. (Year: 2012).*
KR 970009620 Full English Translation. Published Jun. 17, 1997. (Year: 1997).*
KR 20120101897 Full English Translation. Published Sep. 17, 2012. (Year: 2012).*
Office Action dated May 30, 2017 in Japanese Patent Application No. 2015-525168 (with unedited computer generated English translation).
"Quantification of a compound (Lysyl-pyrropyridine) generated in the latter stage of Maillard reaction in a diabetes mouse", Proceedings of Symposium of the Japan Society for Bioscience, Biotechnology, and Agrochemistry, 2008, p. 142, 2B05p03.
"New inspections that draw attention 3. Glomerular filtration function marker 2) Pentosidine", Medical Technology, 2009, vol. 37 No. 6, pp. 576-579.
"Usefulness of pentosidine as bone quality marker", Medical Technology, Apr. 2013, vol. 41 No. 4, pp. 358-359.
Satoshi Takasugi, et al., "A dairy product fermented by lactobacilli cancels the adverse effects of hypochlorhydria induced by a proton pump inhibitor on bone metabolism in growing rats", British Journal of Nutrition, vol. 106, 2011, pp. 1487-1494.

(Continued)

*Primary Examiner* — Renee Claytor
*Assistant Examiner* — Susan E. Fernandez
(74) *Attorney, Agent, or Firm* — Oblon, McClelland, Maier & Neustadt, L.L.P.

(57) ABSTRACT

A pentosidine production inhibitor including a lactic acid bacterium fermentation product as an active ingredient, which has a stronger action and a high safety as a component having an action of inhibiting production of pentosidine.

12 Claims, No Drawings

(56) References Cited

OTHER PUBLICATIONS

Manisha N. Ashar, et al., "Fermented milk containing ACE-inhibitory peptides reduces blood pressure in middle aged hypertensive subjects", Milchwissenschaft, vol. 59 No. 7/8, 2004, pp. 363-366.
Satoshi Sugiyama, et al., "Plasma levels of pentosidine in diabetic patients: an advanced glycation end product", Journal of the American Society of Nephrology, vol. 9., 1998, pp. 1681-1688.
Izawa et al., "effects of fermentation conditions and soybean peptide supplementation on hyaluronic acid production by *Streptococcus thermophilus* strain YIT 2084 in milk," Journal of Bioscience and Bioengineering, vol. 109, No. 4, (2010), pp. 356-360.
International Search Report dated Sep. 22, 2014 in PCT/JP14/066799 filed Jun. 25, 2014.

* cited by examiner

PENTOSIDINE PRODUCTION INHIBITOR

TECHNICAL FIELD

The present invention relates to a pentosidine production inhibitor including a lactic acid bacterium fermentation product as an active ingredient.

BACKGROUND ART

Pentosidine is an advanced glycation end product (AGE) that has a structure in which a lysine residue and an arginine residue are crosslinked via a pentose.

Pentosidine is accumulated on human dura mater and skin collagen. A high level of pentosidine is sometimes also detected in a patient of rheumatism or severe atopic dermatitis, and relations with those diseases have been suggested.

Accordingly, such pentosidine-related diseases can be prevented and treated by inhibiting production of pentosidine.

However, while Edaravone (PTL 1) and the like have been hitherto known as a component having an action of inhibiting the pentosidine production, the effect, safety, and the like have not been fully satisfactory.

CITATION LIST

Patent Literature

PTL 1: JP-A-2004-300153

SUMMARY OF INVENTION

Technical Problem

Accordingly, an object of the present invention is to provide a component having an action of inhibiting pentosidine production that has a stronger action and a high safety.

Solution to Problem

As a result of intensive study to solve the above problem, the present inventors have found that a lactic acid bacterium fermentation product surprisingly has the action of inhibiting pentosidine production. Furthermore, the present inventors have found that when a lactic acid bacterium fermentation product obtained by fermenting a culture medium containing a milk constituent or an aloe with a lactic acid bacterium is used as an active ingredient among other lactic acid bacterium fermentation products, the action of inhibiting pentosidine production is higher, thereby accomplishing the present invention.

Specifically, the present invention is directed to a pentosidine production inhibitor including a lactic acid bacterium fermentation product as an active ingredient.

The present invention is also directed to a pentosidine production inhibitor including as an active ingredient a lactic acid bacterium fermentation product obtained by fermenting a culture medium containing a milk constituent with a lactic acid bacterium.

The present invention is further directed to a pentosidine production inhibitor including as an active ingredient a lactic acid bacterium fermentation product obtained by fermenting a culture medium containing an aloe with a lactic acid bacterium.

The present invention is further directed to a method for inhibiting pentosidine production in human, characterized in that the pentosidine production inhibitor including a lactic acid bacterium fermentation product as an active ingredient is administered to a human.

Advantageous Effects of Invention

The pentosidine production inhibitor of the present invention exhibits a strong action even in a low concentration, and is also highly safe since it originates in a natural product, and therefore can achieve prevention and treatment of pentosidine-related diseases.

DESCRIPTION OF EMBODIMENT

The pentosidine production inhibitor of the present invention (hereinafter referred to as "the inhibitor of the invention") includes a lactic acid bacterium fermentation product as an active ingredient. As used herein, the lactic acid bacterium fermentation product refers to a product obtained by fermenting a raw material that can be fermented by a lactic acid bacterium with the lactic acid bacterium. The lactic acid bacterium fermentation product may contain or may not contain a lactic acid bacterium, and includes a supernatant or the like obtained by removing a lactic acid bacterium from a cultured product of the lactic acid bacterium by filtration or the like.

As used herein, the pentosidine production inhibition means to reduce the amount of pentosidine produced, and the pentosidine production inhibition rate is a value calculated by measuring and comparing respective amounts of pentosidine produced in the presence and absence of a test sample in a substrate solution obtained by mixing equal amounts of ribose, lysine hydrochloride, and arginine hydrochloride, in accordance with a method described in an article (D. R. Sell and V. M. Monnier, J. Biol. Chem 264, 21597-21602, (1989)). More specifically, the test sample is mixed with a substrate solution obtained by mixing equal amounts of ribose, lysine hydrochloride, arginine hydrochloride and allowed to react at 60° C. for 24 hours. The mixture is then irradiated with 330 nm excitation light, and the intensity of the generated 390 nm fluorescent light is measured. The pentosidine production inhibition rate is calculated using [Math. 1] shown in Examples described later.

A raw material of the lactic acid bacterium fermentation product is not particularly limited as long as it can be fermented by a lactic acid bacterium, and examples thereof include a culture medium containing a raw material derived from a plant, such as aloe and soy milk, and a raw material derived from an animal, such as animal milk, for example, cow's milk, human's milk, and goat's milk, a cream, and a skim milk powder, and a culture medium for a lactic acid bacterium such as MRS (Man, Rogosa and Sharpe) medium and M-17 medium. Among the raw materials, a culture medium containing a milk constitute such as animal milk, for example, cow's milk, human's milk, and goat's milk, a cream, and a skim milk powder, or a culture medium containing an aloe are particularly preferably used. The raw materials may be subjected to filtration; centrifugation; dissolution or dilution with a solvent; pulverization by a mixer, etc.; an enzymatic treatment by an amylase, a cellulase, a pectinase, a protease, etc.; or extraction with a solvent.

The lactic acid bacterium used for the fermentation is also not particularly limited, and examples thereof include genus *Lactobacillus* bacteria such as *Lactobacillus casei, Lactobacillus crispatus, Lactobacillus plantarum, Lactobacillus amylovorus, Lactobacillus brevis, Lactobacillus buchneri,*

*Lactobacillus fermentum, Lactobacillus mall, Lactobacillus parabuchneri, Lactobacillus paracasei, Lactobacillus pentosus, Lactobacillus rhamnosus, Lactobacillus vitulinus*, and *Lactobacillus zeae*; genus *Lactococcus* bacteria such as *Lactococcus lactis*; genus *Leuconostoc* bacteria such as *Leuconostoc mesenteroides, Leuconostoc carnosum, Leuconostoc citreum, Leuconostoc gelidum*, and *Leuconostoc lactis*; genus *Pediococcus* bacteria such as *Pediococcus pentosaceus*; genus *Enterococcus* bacteria such as *Enterococcus faecalis* and *Enterococcus faecium*; genus *Weissella* bacteria such as *Weissella confusa, Weissella paramesenteroides*, and *Weissella viridescens*; and genus *Streptococcus* bacteria such as *Streptococcus thermophilus*. One of or two or more of the lactic acid bacteria may be used.

The condition where a culture medium containing a raw material as described above is fermented by a lactic acid bacterium is not particularly limited and, for example, the culture medium may be inoculated with a lactic acid bacterium at 0.01 to 10% by mass, preferably 0.1 to 5% by mass, and cultured at 20 to 45° C., preferably 25 to 42° C. for 1 to 96 hours, preferably 3 to 96 hours.

In addition, in the fermentation, for example, a yeast extract, a chlorella extract, a vitamin, a protein degradation product, an amino acid, a mineral, a salt, a surfactant, a fatty acid, a metal, or the like may be added to the culture medium.

The lactic acid bacterium fermentation product obtained as described above may be used as it is as the inhibitor of the invention, but may be subjected to a known purification or separation treatment, such as filtration, dialysis, precipitation, and centrifugation, and may be further subjected to extraction with a solvent or heating, prior to use. Lyophilization or inspissation may also be applied.

The thus obtained lactic acid bacterium fermentation product has a high activity of inhibition of pentosidine production, and the pentosidine production inhibition rate is 25% or higher, preferably 26 to 60% when the concentration of the lactic acid bacterium fermentation product is 0.05% by mass in terms of the dry solid content.

As a preferred embodiment of the lactic acid bacterium fermentation product used in the present invention, there are mentioned a product obtained by fermenting a culture medium containing a milk constituent with a lactic acid bacterium, or a product obtained by fermenting a culture medium containing an aloe with a lactic acid bacterium. Incidentally, the aloe, as used herein, includes not only aloe itself but also a component derived from aloe. Among the lactic acid bacterium fermentation products obtained by fermenting a culture medium containing a milk constituent with a lactic acid bacterium, preferred is a supernatant obtained from a fermentation product of a culture medium containing a milk constituent by a lactic acid bacterium, and particularly preferred are a low molecular fraction of a supernatant obtained from a fermentation product of a culture medium containing a milk constituent by a lactic acid bacterium and a high molecular fraction of a supernatant obtained from a fermentation product of a culture medium containing a milk constituent by a lactic acid bacterium. In addition, as the lactic acid bacterium fermentation product obtained by fermenting a culture medium containing an aloe with a lactic acid bacterium, preferred is a supernatant obtained from a fermentation product of a culture medium containing an aloe by a lactic acid bacterium.

Hereinafter, as a preferred embodiment of the lactic acid bacterium fermentation product used in the present invention, a product obtained by fermenting a culture medium containing a milk constituent with a lactic acid bacterium and a product obtained by fermenting a culture medium containing an aloe with a lactic acid bacterium will be described.

As a lactic acid bacterium used for a product obtained by fermenting a culture medium containing a milk constituent with a lactic acid bacterium (hereinunder may be referred to as "lactic acid bacterium fermentation product (milk constituent)"), for example, a lactic acid bacterium of genus *Streptococcus* such as *Streptococcus thermophilus*, and one of genus *Lactobacillus* such as *Lactobacillus casei* and *Lactobacillus plantarum* are preferred. Among the lactic acid bacteria, a lactic acid bacterium of a genus *Streptococcus* is preferred, and *Streptococcus thermophilus* is more preferred. Among them, *Streptococcus thermophilus* strain YIT2084 (FERM BP-10879, date of deposit: Aug. 18, 2006), *Streptococcus thermophilus* strain YIT2085 (FERM BP-10880, date of deposit: Aug. 18, 2006), *Streptococcus thermophilus* strain YIT2021 (FERM BP-7537, date of deposit: Nov. 1, 1996), *Streptococcus thermophilus* strain YIT2059 (FERM BP-10878, date of deposit: Aug. 18, 2006), *Streptococcus thermophilus* strain YIT2001 (FERM BP-7538, date of deposit: Jan. 31, 2001) and the like are preferred, and *Streptococcus thermophilus* strain YIT2084 (FERM BP-10879, date of deposit: Aug. 18, 2006) are particularly preferred. Incidentally, one of or two or more of the lactic acid bacteria may be used. The lactic acid bacterium strains of the above deposit numbers had been deposited to International Patent Organism Depositary, National Institute of Advanced Industrial Science and Technology (Central 6, 1-1, Higashi 1-chome, Tsukuba-shi, Ibaraki-ken, 305-8566 Japan), which has been succeeded since Apr. 1, 2013 by International Patent Organism Depositary, National Institute of Technology and Evaluation (Room 120, 2-5-8 Kazusakamatari, Kisarazu-shi, Chiba-ken, 292-0818 Japan).

The fermentation of a culture medium containing a milk constituent by a lactic acid bacterium may be carried out in accordance with a known culture condition. For example, a culture medium adjusted with water so as to have 1 to 20% by mass of a milk constituent may be inoculated with a lactic acid bacterium at 0.01% by mass to 10% by mass, preferably 0.1% by mass to 5% by mass, and cultured at 20° C. to 45° C., preferably at 37° C. to 42° C. for 1 hour to 48 hours, preferably 4 hours to 30 hours. Incidentally, as the culture condition at this time, allowing to stand, stirring, shaking, ventilation, etc. are exemplified. A method suitable for the culture may be appropriately selected therefrom and used for the culture.

A generally used component may be additionally added to the culture medium containing a milk constituent for the purpose of compensating source of nutrients in culturing the lactic acid bacterium. Examples of the component include a yeast extract, a chlorella extract, a vitamin such as vitamin A, a vitamin B, vitamin C, and vitamin E, protein degradation products including different peptides, an amino acid, a salt of calcium, magnesium, etc., a surfactant such as polysorbate 80, a fatty acid such as oleic acid, a metal such as calcium, magnesium, and manganese, and the like.

The thus obtained lactic acid bacterium fermentation product (milk constituent) may be subjected to a known purification or separation treatment such as filtration, dialysis, precipitation, and centrifugation, and may be further subjected to extraction with a solvent, etc., heating, lyophilization or inspissation.

Among other lactic acid bacterium fermentation products (milk constituent), the inhibiter of the invention is preferably a supernatant obtained from a fermentation product of a culture medium containing a milk constituent by a lactic acid bacterium, particularly preferably a low molecular fraction of a supernatant obtained from a fermentation product of a culture medium containing a milk constituent by a lactic acid bacterium or a high molecular fraction of a supernatant obtained from a fermentation product of a culture medium containing a milk constituent by a lactic acid bacterium.

The supernatant obtained from a fermentation product of a culture medium containing a milk constituent by a lactic acid bacterium (hereinafter may be referred to as "lactic acid bacterium fermentation product (milk constituent) supernatant") can be produced by removing solid matter from a lactic acid bacterium fermentation product (milk constituent) obtained as described above in accordance with an ordinary method such as centrifugation and filtration.

The low molecular fraction of a supernatant obtained from a fermentation product of a culture medium containing a milk constituent by a lactic acid bacterium (hereinafter may be referred to as "low molecular fraction of lactic acid bacterium fermentation product (milk constituent) supernatant") refers to a fraction of the lactic acid bacterium fermentation product (milk constituent) supernatant having a molecular weight of 20,000 Da or lower. The fraction having a molecular weight of 20,000 Da or lower can be taken by subjecting the lactic acid bacterium fermentation product (milk constituent) supernatant to a treatment such as ultrafiltration, gel filtration, and dialysis.

The thus obtained low molecular fraction of a lactic acid bacterium fermentation product (milk constituent) supernatant has a pentosidine production inhibition rate of 25% or higher, preferably 26 to 40% when the concentration thereof is 0.05% by mass in terms of the dry solid content.

The high molecular fraction of a supernatant obtained from a fermentation product of a culture medium containing a milk constituent by a lactic acid bacterium (hereinafter may be referred to as "high molecular fraction of lactic acid bacterium fermentation product (milk constituent) supernatant") refers to a fraction of the lactic acid bacterium fermentation product (milk constituent) supernatant having a molecular weight of 3,500 Da or higher. The fraction having a molecular weight of 3,500 Da or higher can be taken by subjecting the lactic acid bacterium fermentation product (milk constituent) supernatant to a treatment such as ultrafiltration, gel filtration, and dialysis. Incidentally, in this case, a protein such as casein contained in the lactic acid bacterium fermentation product is preferably precipitated in advance with trichloroacetic acid, ethanol, or the like in the removal of the solid matter. This process allows for the high molecular fraction of a supernatant of the lactic acid bacterium fermentation product to contain a large amount of polysaccharides. In the case where the high molecular fraction containing a larger amount of polysaccharides is desired, it is particularly preferred that, in the fermentation of a culture medium containing a milk constituent by a lactic acid bacterium, the medium is cultured under a condition of pH 6 to 8 at 37 to 40° C. The pH of the culture medium may be adjusted using sodium hydroxide or the like.

The thus obtained high molecular fraction of a lactic acid bacterium fermentation product (milk constituent) supernatant has a pentosidine production inhibition rate of 25% or higher, preferably 35 to 60% when the concentration thereof is 0.05% by mass in terms of the dry solid content.

On the other hand, a product obtained by fermenting a culture medium containing an aloe with a lactic acid bacterium (hereinafter may be referred to as "lactic acid bacterium fermentation product (aloe)") may be obtained, for example, by culturing a lactic acid bacterium in a culture medium containing an aloe as described above.

Aloe which is contained in the culture medium is a generic name of a Liliaceae plant native of Africa, and includes not less than 300 varieties such as *Aloe arborescens* and *Aloe vera*. It is known that an aloe contains a large amount of polysaccharides such as mucin and aloe mannan, and also contains components such as aloin, aloenin, aloecin, alomicin, and aloeulcin. The aloe used in the present invention is not particularly limited as long as it is in the aloe family, but in particular, *Aloe arborescens* and *Aloe vera* is preferably used from the viewpoint of the availability and the cost. The used part in the aloe is not particularly limited, and in addition to the leaf, mesophyll, bud and root, the juice and dripping liquid of the part above, various components obtained therefrom, and the like, which contribute to easiness of the subsequent production steps because of not containing a fiber component, may be used.

Incidentally, a lactic acid bacterium can not assimilate the fiber component, the protein component, and the like in the aloe, and therefore the aloe preferably subjected to a degradation treatment and the like such as a cellulase treatment and a protease treatment in accordance with an ordinary method prior to the fermentation. When a cellulase treatment is performed, the assimilation ability is enhanced to promote the fermentation and the non-assimilated cellulose or the like does not remain in the lactic acid bacterium fermentation product, leading to the easiness of the subsequent production steps. When a protease treatment is performed, a protein component or the like does not remain in the lactic acid bacterium fermentation product, not causing cloudiness, and therefore a clarification step is not required after the fermentation. When an amylase treatment is further applied, the assimilation ability of the lactic acid bacterium is enhanced. For an enzymolysis treatment, one of or two or more of: a fiber material degrading enzyme (a cellulase) such as cellulase and pectinase; a proteolytic enzyme (a protease) such as an acidic protease, a neutral protease, an alkaline protease, a proteinase such as papain, ficin, and bromelain, a peptidase, and a mannanase; and an amylolytic enzyme (an amylase) such as an $\alpha$-amylase and a glucoamylase, may be appropriately selected and used. From the viewpoints of not impairing the palatability of the lactic acid bacterium fermentation product and of fully assimilating the aloe, no saccharide is preferably added to the aloe.

As the lactic acid bacterium for use in the fermentation, a lactic acid bacterium of genus *Lactobacillus* is preferred, and *Lactobacillus plantarum* is more preferred. One of or two or more of the lactic acid bacteria may be used.

The fermentation of a culture medium containing an aloe by a lactic acid bacterium may be conducted in accordance with a known culture condition. For example, an aloe extract in which the Brix is adjusted to 3.0 or higher and the pH is adjusted to 4.2 or lower may be inoculated with a lactic acid bacterium at 0.01% by mass to 10% by mass, preferably 0.1% by mass to 5% by mass, and cultured at 20° C. to 40° C., preferably 25° C. to 40° C., for 6 hours to 96 hours, preferably 24 hours to 96 hours. As other culture conditions in this fermentation, allowing to stand, stirring, shaking, ventilation, and the like are exemplified. A method suitable for the culture may be appropriately selected therefrom and used for the culture.

To the culture medium containing an aloe, a generally used component other than saccharides may be additionally added for the purpose of compensating source of nutrients in culturing the lactic acid bacterium. Examples of the component include a yeast extract, a chlorella extract, a vitamin such as vitamin A, a vitamin B, vitamin C, and vitamin E, protein degradation products including different peptides, an amino acid, a salt of calcium, magnesium, etc., a surfactant such as polysorbate 80, a fatty acid such as oleic acid, a metal such as calcium, magnesium, and manganese, and the like.

The thus obtained lactic acid bacterium fermentation product (aloe) may be subjected to a known purification or separation treatment such as filtration, dialysis, precipitation, and centrifugation, and may be further subjected to extraction with a solvent, etc., heating, lyophilization or inspissation.

The inhibiter of the invention is particularly preferably a supernatant obtained from a fermentation product of a culture medium containing an aloe by a lactic acid bacterium among the lactic acid bacterium fermentation products (aloe).

The supernatant obtained from a fermentation product of a culture medium containing an aloe by a lactic acid bacterium (hereinafter referred to as "lactic acid bacterium fermentation product (aloe) supernatant") can be produced by removing solid matter from the lactic acid bacterium fermentation product (aloe) obtained as describe above in accordance with an ordinary method such as centrifugation and filtration.

The thus obtained supernatant obtained from a fermentation product of a culture medium containing an aloe by a lactic acid bacterium has a pentosidine production inhibition rate of 25% or higher, preferably 28 to 50% when the concentration thereof is 0.05% by mass in terms of the dry solid content.

The inhibiter of the invention described above may be incorporated in a skin external preparation such as a cosmetic, a medicine, and a quasi-drug to make, for example, a basic cosmetic such as a lotion, a milky lotion, a cream, a facial pack, and an essence; a hair care product such as a shampoo, a hair rinse, a hair treatment, a hair tonic, a hair liquid, a hair cream, and a hair milk; a bath preparations such as a bath additive; a makeup cosmetic such as a foundation, a lipstick, a mascara, and an eye shadow; and a special cosmetic such as a sun screen. An amount of the lactic acid bacterium culture supernatant to be incorporated as the pentosidine production inhibitor of the present invention is not particularly limited and may be appropriately set depending on the form of the skin external preparation, and the like. The amount is preferably 0.003% by mass to 1% by mass, more preferably 0.015% by mass to 0.6% by mass, particularly preferably 0.03% by mass to 0.3% by mass in terms of the dry solid content.

In the skin external composition, a known component used in the field of cosmetic, medicine, quasi-drug, and the like may be added to the extent that the effect of the present invention is not impaired. Examples of the known component include water, an alcohol, an oil component, a surfactant, a preservative, a fragrance, a pigment, a humectant, a thickener, an antioxidant, a chelating agent, a pH modifier, a foaming agent, a UV absorbing and scattering agent, a powder, a vitamin, an amino acid, an antimicrobial agent, a plant extract, a seaweed extract, and a medicament.

The inhibiter of the invention can be prepared by forming the lactic acid bacterium fermentation product into a preparation as it is or in combination with a known pharmaceutical carrier.

Furthermore, the inhibiter of the invention, which includes a lactic acid bacterium fermentation product having a food experience as an active ingredient, can also be incorporated in various drinks and foods. For example, after an appropriate auxilially is added to the lactic acid bacterium fermentation product, the mixture may be shaped using a common means into a form suitable for a food such as, for example, a form of granule, particle, tablet, capsule, and paste to be subjected to eating. Alternatively, the inhibiter of the invention may be used by adding it to various foods, for example, a processed mead product such as hum and sausage, a processed seafood product such as kamaboko and chikuwa, bread, and a confectionary, or may be used by adding it to a drink such as water, a fruit juice, milk, and a beverage.

The inhibiter of the invention described above can inhibit production of pentosidine in human when being administered to human, and thus can prevent and treat pentosidine-related diseases. A method for administering the inhibiter of the invention to human is not particularly limited, and for example, the inhibiter of the invention of an amount enabling the prevention and treatment may be administered to a site of human body where pentosidine is produced, through an administration route suitable for the site. Examples of the site where pentosidine is produced include skin and dura mater. Examples of the administration route suitable for the site include application on the site, oral administration, and injection.

EXAMPLES

The present invention will be described in detail below with reference to examples. The present invention is by no means limited to the examples.

Example 1

Pentosidine Production Inhibition Activity of Low Molecular Fraction of Lactic Acid Bacterium Fermentation Product (Milk Constituent) Supernatant:

One platinum loop of a bacterial strain of *Streptococcus thermophilus* strain YIT2084 (FERM BP-10879) stored at −80° C. was inoculated into M-17 culture medium (manufactured by Difco) containing 10 g/L of lactose in a 2 mL test tube, and the medium was allowed to stand at 40° C. over night to culture the strain. Subsequently, the cultured product was inoculated into 2 mL of a 10 mass % aqueous skim milk powder solution (manufactured by Difco) at 1% by mass, and then the solution was allowed to stand at 40° C. over night to culture the strain. This procedure was designated as a preculture. Then, the precultured product was inoculated into 100 mL of a main culture medium (a 3 mass % aqueous skim milk powder solution) at 1% by mass, and the medium was allowed to stand at 40° C. for 24 hours to culture the strain. The bacterial suspension after culturing was subjected to centrifugation at 4° C. and 8,000×g for 15 minutes and the precipitate was removed. The resulting precipitation-removed liquid (supernatant) was subjected to ultrafiltration at 4° C. and 3,000×g for 1 hour using a centrifugal ultrafiltration filter whose molecular weight cutoff was 20.000 Da (Centricut Mini V-20: manufactured by Kurabo Industries), whereby 10 mL of a low molecular fraction was obtained. The low molecular fraction had a dry solid content of 2% (20,000 µg/mL). The average molecular weight of the low molecular fraction of the lactic acid bacterium fermentation product (milk constituent) supernatant was approximately 300 Da.

Incidentally, the average molecular weight was measured by dissolving the low molecular fraction in a 50 mM sodium chloride solution and subjecting the solution to HPLC under the following conditions.

[HPLC Conditions]
Apparatus: Waters-600E
Detector: ISI RI-980
Column: Shodex SUGARKS-804
Column temperature: 80° C.
Mobile phase: 50 mM NaCl
Flow rate: 1 mL/min
Injection volume: 10 μL The pentosidine production inhibition rate (%) of the low molecular fraction obtained above was calculated from the amount of the produced pentosidine. First, a mixture of equal amounts of 50 mM ribose, 50 mM lysine hydrochloride, 50 mM arginine hydrochloride, and 100 mM sodium phosphate buffer solution (pH 7.4) was provided as a substrate solution. Next, a test sample solution prepared by diluting the low molecular fraction obtained above with a 100 mM sodium phosphate buffer solution (pH 7.4) was mixed with the substrate solution in a ratio of substrate solution to the test sample solution of 5/1, and the mixture was reacted in a thermostat chamber of 60° C. for 24 hours. As a control, the same reaction except for using water instead of the low molecular fraction was carried out. As a blank, a buffer solution containing none of ribose, lysine, and arginine was used. After the completion of the heating, the test sample was irradiated with 330 nm excitation light, and the intensity of the generated 390 nm fluorescent light was measured, and the amount of the produced pentosidine was calculated as the fluorescence level. From the fluorescence intensity, the pentosidine production inhibition rate was calculated by the following formula. The results are shown in Table 1.

$$\text{Pentosidine production inhibition rate (\%)} = ((Ec-Eb)-(Es-Eb))/(Ec-Eb) \times 100 \quad [\text{Math. 1}]$$

Es: fluorescence intensity of sample
Ec: fluorescence intensity of control
Eb: fluorescence intensity of blank

TABLE 1

| Concentration of low molecular fraction of lactic acid bacterium fermentation product (milk constitute) supernatant (in terms of dry solid content) | Pentosidine production inhibition rate |
|---|---|
| 0.05 mass % | 26.6% |
| 0.2 mass % | 38.3% |

It was found from the above results that the low molecular fraction of the lactic acid bacterium fermentation product (milk constituent) supernatant showed a high pentosidine production inhibition rate at a low concentration of 0.05% by mass. In addition, it was also confirmed that the pentosidine production inhibition rate was increased in a concentration dependent manner.

Example 2

Pentosidine Production Inhibition Activity of High Molecular Fraction of Lactic Acid Bacterium Fermentation Product (Milk Constituent) Supernatant:

One platinum loop of *Streptococcus thermophilus* strain YIT2084 (FERM BP-10879) stored at −80° C. was inoculated into M-17 Culture medium (manufactured by Difco) containing 10 g/L of lactose in a 2 mL test tube, and the medium was allowed to stand at 40° C. over night to culture the strain. Subsequently, the cultured product was inoculated into 2 mL of a 10 mass % aqueous skim milk powder solution (manufactured by Difco) at 1% by mass, and then the solution was allowed to stand at 40° C. over night to culture the strain. This procedure was designated as a preculture. Then, the precultured product was inoculated into 1 L of a main culture medium (a 10 mass % aqueous skim milk powder solution containing 1% soy bean peptide) prepared in a jar fermentor at 0.1% by mass, and cultured at 40° C. for 24 hours under a condition of a rotating speed of 100 rpm while maintaining the pH of the culture medium at 7 with a 8N sodium hydroxide solution. Next, after cooling the resultant in ice, trichloroacetic acid (TCA) was added at a final concentration of 10% w/v, and the mixture was allowed to stand at 4° C. for 2 hours. After centrifugation at 18,300×g for 30 minutes, the equal amount of a cold 99 mass % ethanol was added to the supernatant, and further allowed to stand at 4° C. over night. After dialysis by a dialysis tube (Spectra/Por Membrane (MW 3,500): manufactured by Spectrum Medical), the resulting high molecular fraction was subjected to lyophilization in accordance with an ordinary method. The high molecular fraction of the lactic acid bacterium fermentation product (milk constituent) supernatant had an average molecular weight of approximately 900,000 Da. The method for measuring the average molecular weight is the same as for the low molecular fraction of the lactic acid bacterium fermentation product (milk constituent) supernatant.

As for the high molecular fraction of the lactic acid bacterium fermentation product (milk constituent) supernatant obtained above, the pentosidine production inhibition rate (%) was calculated in the same manner as in Example 1. The results are shown in Table 2.

TABLE 2

| Concentration of high molecular fraction of lactic acid bacterium fermentation product (milk constitute) supernatant (in terms of dry solid content) | Pentosidine production inhibition rate |
|---|---|
| 0.025 mass % | 23.8% |
| 0.05 mass % | 45.4% |

It was found from the above results that the high molecular fraction of the lactic acid bacterium fermentation product (milk constituent) supernatant also showed a high pentosidine production inhibition rate at a low concentration of 0.05% by mass. In addition, it was also confirmed that the pentosidine production inhibition rate was increased in a concentration dependent manner.

Example 3

Pentosidine Production Inhibition Activity of Lactic Acid Bacterium Fermentation Product (*Aloe*) Supernatant:

Frozen leaves of *Aloe vera* (botanical name: *Aloe barbadensis* Miller) were thawed and pulverized, two parts of water and 0.05% by mass of citric acid were added, and a cellulase ((cellulase "Onozuka" 3S: manufactured by Yakult Pharmaceutical Industry)) was allowed to act on the mixture at 40° C. for 3 hours. The mixture was then heated to 90° C. once, and cooled to room temperature, filtrated, and concentrated under a reduced pressure until Brix 3.5 was given, whereby an *Aloe vera* extract was obtained. The obtained *Aloe vera* extract (pH 3.7) was heated at 100° C. for 100 minutes for sterilization. The *Aloe vera* extract was inoculated with the precultured liquid of a *Lactobacillus plantarum* standard strain (ATCC 14917) at 1%, and allowed to stand at 30° C. for 72 hours to culture the strain. After the culturing, the filtrate was taken by filtration to obtain a lactic acid bacterium fermentation product (aloe) supernatant. The lactic acid bacterium fermentation product (aloe) supernatant had a dry solid content of 2.9% (29,000 μg/mL).

As for the lactic acid bacterium fermentation product (aloe) supernatant obtained above, the pentosidine production inhibition rate (%) was calculated in the same manner as in Example 1. As for an *Aloe vera* extract that was not fermented by *Lactobacillus plantarum*, the pentosidine production inhibition rate (%) was also calculated in the same manner. The results are shown in Tables 3 and 4.

TABLE 3

| Concentration of lactic acid bacterium fermentation product (*aloe*) supernatant (in terms of dry solid content) | Pentosidine production inhibition rate |
|---|---|
| 0.05 mass % | 29.2% |
| 0.0725 mass % | 44.4% |
| 0.145 mass % | 60.7% |
| 0.29 mass % | 81.8% |

TABLE 4

| Concentration of *Aloe vera* extract (in terms of dry solid content) | Pentosidine production inhibition rate |
|---|---|
| 0.05 mass % | 20.3% |
| 0.0725 mass % | 22.0% |

It was found from the above results that the lactic acid bacterium fermentation product (aloe) supernatant had a higher pentosidine production inhibition rate by 1.4 times or more at a low concentration of 0.05% by mass, compared with an *Aloe vera* extract that was not fermented by *Lactobacillus plantarum* In addition, the pentosidine production inhibition rate was increased in a concentration dependent manner.

Example 4

Preparation of Lotion:
A lotion having a composition shown in Table 5 below was prepared. The lotion was prepared by adding components 1 to 6 to component 7 and fully stirring the mixture.

TABLE 5

| Component | Raw material | Amount (mass %) |
|---|---|---|
| 1 | Ethanol | 5.0 |
| 2 | 1,3-Butyleneglycol | 2.0 |
| 3 | Polyoxyethylene hydrogenated castor oil | 0.05 |
| 4 | Methyl parahydroxybenzoate | 0.1 |
| 5 | Fragrance | 0.1 |
| 6 | Lactic acid bacterium fermentation product* | 10.0 |
| 7 | Distilled water | Balance to give 100 in total |

*The low molecular fraction of lactic acid bacterium fermentation product (milk constitute) supernatant obtained in Example 1 was used as it was.

Example 5

Preparation of Milky Lotion:
A milky lotion having a composition shown in Table 6 below was prepared. The milky lotion was prepared as follows. Components 7, 8 and 10 were added to component 11, the mixture was heated, components 1 to 6 were added at 80° C., and the mixture was emulsified. Component 9 was then added, and the mixture was stirred and cooled to a room temperature.

TABLE 6

| Component | Raw material | Amount (mass %) |
|---|---|---|
| 1 | Stearic acid | 2.0 |
| 2 | Liquid paraffin | 5.0 |
| 3 | Squalane | 2.0 |
| 4 | Sorbitan monostearate | 0.05 |
| 5 | Polyoxyethylene(20)sorbitan monostearate | 2.0 |
| 6 | Butyl parahydroxybenzoate | 0.05 |
| 7 | Glycerol | 2.0 |
| 8 | Methyl parahydroxybenzoate | 0.1 |
| 9 | Fragrance | 0.15 |
| 10 | Lactic acid bacterium fermentation product* | 0.1 |
| 11 | Distilled water | Balance to give 100 in total |

*The high molecular fraction of lactic acid bacterium fermentation product (milk constitute) supernatant obtained in Example 2 was used as it was.

Example 6

Preparation of Cream:
A cream having a composition shown in Table 7 below was prepared. The cream was prepared as follows. Components 9, 10 and 12 were added to component 13, the mixture was heated, components 1 to 8 were added at 80° C. and the mixture was emulsified. Component 11 was then added, and the mixture was stirred and cooled to a room temperature.

TABLE 7

| Component | Raw material | Amount (mass %) |
|---|---|---|
| 1 | Liquid paraffin | 23.0 |
| 2 | Petrolatum | 7.0 |
| 3 | Cetanol | 1.0 |
| 4 | Stearic acid | 2.0 |
| 5 | Bees wax | 2.0 |
| 6 | Sorbitan monostearate | 3.5 |
| 7 | Polyoxyethylene(20)sorbitan monostearate | 2.5 |
| 8 | Butyl parahydroxybenzoate | 0.05 |
| 9 | 1,3-Butyleneglycol | 1.0 |
| 10 | Methyl parahydroxybenzoate | 0.1 |
| 11 | Fragrance | 0.15 |
| 12 | Lactic acid bacterium fermentation product* | 5.0 |
| 13 | Distilled water | Balance to give 100 in total |

*The lactic acid bacterium fermentation product (aloe) supernatant obtained in Example 3 was use as it was.

INDUSTRIAL AVAILABILITY

The pentosidine production inhibitor of the present invention can be used for prevention and treatment of pentosidine-related diseases.

The invention claimed is:
1. A method for inhibiting pentosidine production in a human subject comprising contacting the human subject with a pentosidine production inhibitor composition that consists of a pharmaceutically acceptable carrier and a fraction of a supernatant, as an active ingredient, obtained from a fermentation product of a cultured medium containing a milk constituent with a lactic acid bacterium as an active ingredient, wherein the fraction has a molecular weight of not more than 20,000 Da, wherein a pentosidine production inhibition rate is 25% or higher when the concentration of the fraction is 0.05% by mass in terms of the dry solid content, wherein the relative amount of pentosidine in a test sample prepared by combining a sample obtained from the human subject to a solution is determined by fluorescence and the pentosidine production inhibition rate (%) is given by [Math. 1]:

$$((Ec-Eb)-(Es-Eb))/(Ec-Eb)\times 100, \text{ wherein}$$

Es is the fluorescence intensity of the test sample,

Ec is the fluorescence intensity of the control sample that does not contain pentosidine and contains the same solution as the test sample, and Eb is the fluorescence intensity of a blank sample that does not include ribose, lysine and arginine.

2. The method of claim 1, wherein the pentosidine production inhibitor is contacted with the skin or dura mater.

3. The method of claim 1, wherein the human subject has a pentosidine-related disease.

4. The method of claim 1, therein the human subject has rheumatism or atopic dermatitis.

5. The method of claim 1, wherein the lactic acid bacterium is *Streptococcus thermophilus*.

6. The method of claim 5, wherein the lactic acid bacterium is a *Streptococcus thermophilus* strain YIT2084 (FERM BP-10879).

7. The method of claim 1, wherein the solution contains 50 mM ribose, 50 mM lysine hydrochloride, 50 mM arginine hydrochloride and 100 mM sodium phosphate buffer solution at pH 7.4 and the solution is contacted with the sample obtained from the human subject at a ratio of 5:1 at 60° C. for 24 hrs and then detecting the relative amount of pentosidine in the test sample Es compared to the control sample Ec, and to the blank sample Eb.

8. A method for inhibiting pentosidine production in a human subject comprising contacting the human subject with a pentosidine production inhibitor comprising a fermentation product, as an active ingredient, obtained from fermenting a culture medium containing an aloe vera extract with a lactic acid bacterium, wherein pentosidine production is inhibited.

9. The method of claim 8, wherein the pentosidine production inhibitor is contacted with the skin or dura mater.

10. The method of claim 8, wherein the human subject has a pentosidine-related disease.

11. The method of claim 8, wherein the human subject has rheumatism or atopic dermatitis.

12. The method of claim 8, wherein the lactic acid bacterium is *Lactobacillus plantarum*.

* * * * *